United States Patent [19]
Khann et al.

[11] 3,945,988
[45] Mar. 23, 1976

[54] PROCESS FOR ISOLATION OF INSULIN FROM PLANT SOURCE

[76] Inventors: Pushpa Khann; Tej Narain Nag; Satish Chandrajain; Suchendra Mohan, all of 74, C, Sarojini Marg C'Scheme, Jaipur, India

[22] Filed: July 16, 1974

[21] Appl. No.: 488,974

[52] U.S. Cl................................. 260/112.7; 195/4
[51] Int. Cl.². ..................... A61K 37/26; C12B 1/20
[58] Field of Search .............................. 260/112.7

[56] References Cited
OTHER PUBLICATIONS
Prout: Metab., 12, 673–686 (1963).
Steiner et al.: Proc. Nat. Acad. Sci. (USA), 57, 473–480 (1967).

Primary Examiner—Elbert L. Roberts
Assistant Examiner—Reginald J. Suyat

[57] ABSTRACT

A method for isolating insulin from the cultured seeds or fruit of Memordica charantia Linn in which the starting material is extracted with ethanol, water and sulfuric acid, adjusting the pH of the extract to 1.5 to 2.0 and then precipitating the insulin by adding cold ethanol and diethyl ether. Zinc traces are added to precipitate the insulin as white crude crystals which are then purified to white needle-like crystals. Comparison of this product with standard insulin by chromatography showed that the present product is substantially the same as the standard insulin.

6 Claims, 1 Drawing Figure

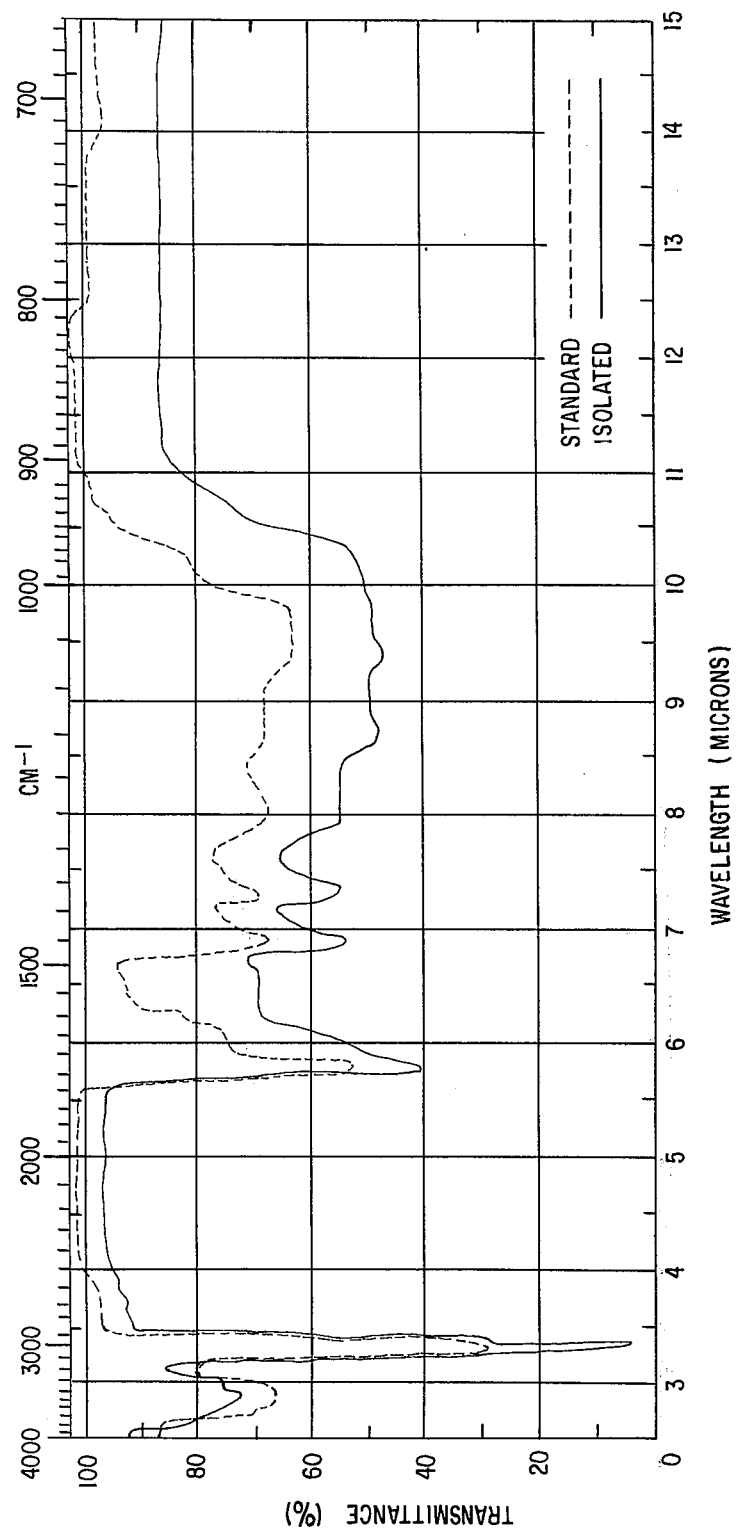

PROCESS FOR ISOLATION OF INSULIN FROM PLANT SOURCE

Insulin has hitherto been extracted from the pancreas of animals but so far there is no report of its isolation from plant materials:

Isolation of Insulin from animal pancreas is open to objection due to the following reasons:
  i. By killing 10,000 animals only 1 pound of pure insulin is obtained.
  ii. If the pancreas is infected by some diseases like cancers etc. there is always a probability of its being carried (if it is a virus along with the insulin).
  iii. Any amount of insulin can be obtained by cultivating plants and thus can be cheaper.

The object of the present invention is to isolate insulin from plant material to avoid the above mentioned drawbacks.

We have found:
  i. That *Memordica charantia* fruits as well as the cultures when subjected to extraction with ethanol yields insulin;
  ii. The cultures established in vitro on revised MS medium and the fruits were used for extracting the insulin;
  iii. That the melting points of the isolated insulin, the mixed melting point of the isolated insulin and the standard sample, the paper and thin layer chromatographic studies of the hydrolyzates of the isolated and the standard samples, the infra red specctral studies of the isolated compound and the standard sample confirmed the presence of insulin in *Memordica charantia*.

According to the present invention, there is provided a process for the isolation of insulin by extraction of an organic material with a mixture of ethanol, water and sulfuric acid, adjusting the pH of the extract to 1.5–2.0 eg., by adding ammonia or hydrochloric acid, precipitating the insulin by adding ethanol and diethyl ether, crystallizing with zinc traces purifying by *tlc* followed if desired by analysis, characterized in that, the organic material used for extraction consists of cultures raised from seed and also fruits of *Memordica charantia* Linn.

Fruits of *M. charantia* collected from the field in the months of April, May and June are preferably used.

The cultures raised on revised (Khanna, P. and Staba, E. J., Lloydia, 1968, 31, 180) Murashige and Skoog's (Murashige, T. and Skoog, F., Physicl. Plantarum, 1962, 15, 470) medium (RT) supplemented with 2,4-dichlorophenoxyacetic acid and 1% agar, the cultures are transferred to liquid RT medium, harvested for extraction of insulin.

The cultures raised on revised (RT: Khanna, P. and Staba, E. J. Lloydia, 1968, 31, 180) Murashige and Skoog's (Murashige, T. and Skoog, F., Physicl. Plantarum, 1968, 15, 470) medium supplemented with 1 ppm of 2,4-dichlorophenoxyacetic acid (2,4-D) and 1% agar, these organised cultures are grown in 100 ml flasks containing 30 ml medium for a period of 36 months and then transferred to liquid medium supplemented with 0.1 ppm of 2,4-D without agar, the liquid cultures are grown on reciprocal horizontal shakers with strokes of 60 rpm. All these cultures were grown at 26°±1°C in 1500–1800 lux incandescent light, after growing cultures in liquid RT medium for 4–6 months on frequent subculturings in fresh RT medium, are harvested for extraction of insulin. Fruits and cultures are separately extracted in ethanol and then mixed with cold ethanol and diethyl ether, needle-like crystals formed by adding zinc in traces after 18 hr. The fruits and cultures are separately crushed, homogenized in water, ethanol and concentrated sulfuric acid adjusting pH 1.5–2.0, filtered, filtrate adjusted to pH 3.0 with ammonia, mixed with cold ethanol, and diethyl ether, kept at 0.5°C for 12 hr. white flocculent precipitate collected, zinc in traces added, kept for 18 hr. formed white crude crystals. The crude crystals are dissolved in 25% ethanol buffered with ammonia and the insulin isolated in pure form by Thin Layer chromatography.

Thin glass plates (20 × 20 cm) coated (0.4 mm to 0.5 mm thick) with silica gel G are activated at 100°C, the solution of insulin applied, the plates developed in n-butanol, water, acetic acid (12:5:2), dried, the single spot corresponding to standard insulin visualized by spraying ninhydrin (0.25% in acetone), isolated along with silica gel G from unsprayed plates, extracted in 25% ethanol buffered with ammonia, and then filtered, the filtrate dried, pure white needle-like crystals formed.

Fruits have 1 gm/100 gram fresh weight of insulin, cultures have 1.90 gm/100 gram fresh weight of insulin.

The analysis is carried out, the isolated substance is hydrolyzed along with the standard insulin, applied on paper chromatograms, developed, yielding same amino acids the isolated substance also containing methionine.

The isolated substance and standard insulin are hydrolyzed separately by 6N HCl for 20 hr. dried, reconstituted in 50% ethanol, applied on Whatman No. 1 filter paper strips, developed in n-butanol, acetic acid, water (60:20:20), strips developed, sprayed with 0.25% ninhydrin in acetone, amino acids same as of standard hydrolyzate.

The analysis is carried out, the fruits and cultures are extracted in ethanol yielding a product which has the same melting point (234°C), infra red spectrum and number of amino acids of the standard insulin as shown in the accompanying graphic drawing.

EXAMPLE 1

The fruits of *M. charantia* were collected from the field during the months of April, May and June. The fresh fruits were crushed in a mortar and extracted for their insulin contents. Hundred grams of the crushed fruits were homogenised in a Waring Blendor with 10 ml distilled water, 45 ml 95% ethanol and 3.6 ml concentrated sulfuric acid for 10-15 min at low speed and 25°-28°C. To this mixture 60 ml distilled water and 250 ml 95% ethanol were added and then homogenized for 15–20 min at low speed. Its pH was adjusted to 1.5–2.0 and the mixture was filtered in vacuo. The pH of the filtrate was adjusted to 3.0 with ammonium hydroxide (28%), mixed with 1.5 L cold absolute ethanol and 2 L diethyl ether and kept at 0.5° for 12 hr. A white white flocculent precipitate (ppt) was obtained after decanting off the supernatant liquid. The crude ppt was washed first with 90 ml acetone, then with 30 ml anhydrous ether and dissolved in 25% ethanol buffered with ammonium hydroxide. Traces of zinc were added to this solution which was then kept at room temperature for 18 hr. Colorless needle-like crystals were formed along with traces of zinc and other impurities. The crude crystals were dissolved in 25% ethanol buffered with ammonium hydroxide for analysis by *tlc*.

Thin glass plates (20 × 20 cm) coated (0.4 mm to 0.5 mm thick) with silica gel G (Kioselgel G nach Stahl, E. Merck) were activated at 100°C for half an hour. The solution containing the isolated substance was applied 1 cm above the edge of the plates along with the standard (insulin) and the plates were run in an organic solvent mixture of n-butanol, water and acetic acid (12:5:2). The developed plates were dried at room temperature and sprayed with 0.25% ninhydrin in acetone. The ninhydrin positive spots ($R_F = 0.19$) corresponding to insulin were isolated from about 200 unsprayed plates along with the silica gel G and extracted with 25% ethanol buffered with ammonia. The extract was filtered and dried in vacuo. Pure colorless crystals thus obtained were weighed (1 g/100 gram fresh weight of fruit).

The melting point of the purified compound (232°–235°) as well as the mmp (234°) were determined. The mp of the standard insulin was recorded as 233°.

The standard insulin as well as the isolated compound were hydrolyzed under reflux with 6N HCl for 20 hr separately. The hydrolyzates were filtered, dried, reconstituted separately in 50% ethanol and applied on strips of Whatman No. 1 paper. The paper strips were run in an organic solvent mixture of n-butanol, water and acetic acid (60 : 20 : 20). The hydrolyzates of both the isolated and the standard insulin were also applied separately along with the known amino acids (hydroxylysine, hydroxypreline, methionine and tryptophan). The various developed chromatograms were sprayed with 0.25% ninhydrin in acetone. The amino acids of the hydrolyzates of the standard coincided exactly with that of the hydrolyzate of the isolated compound except for the presence of methionine in the isolated compound. Hydroxylysine, hydroxypreline, and tryptophen were found to be absent from the hydrolyzate of the isolated compound as well as of the standard hydrolyzate which gave an indication that isolated compound is substantially identical with that of the standard insulin.

The IR spectrum (Perkin-Elmer 337 Grating, spectrophotometer using $COl_4$) of the isolated compound was superimpossable with that of the standard.

The isolated insulin was dissolved (5 mg/ml in sterile distilled water) in sterile injection vials (2 ml) and sealed. The suspension thus formed was shaken well before it was administered to rabbits. The normal blood of the rabbits (each weighing 120–130 gm) was taken and kept in fluoride vials for analysing the level of blood sugar. The isolated insulin (1 ml) was injected intramuscularly to the test animals and blood (1 ml) was taken out after every hour for 3 hours.

The fall in the level of blood sugar was estimated to 20–25% in the first hour and 30–35% each in second and third hour when compared with the normal level of blood sugar of the test animals. Fifty such cases were examined and the mean values taken.

EXAMPLE 2

The seeds of *M. charantia* were notched with a scalpal at the micropylar end, sterilized with 5.25% sodium hypochlorite solution in sterile distilled water, shaken for 5–10 min and then, rinsed three times with sterile water.

The sterile seeds were inoculated in 100 ml flasks containing 30 ml of modified (MT; Khanna, P. and Staba, E. J. Lloydia, 1968, 31, 180) Murashige and Skoog's (Murashige, T. and Skoog, F. Physiol. Plantarum 1962, 15, 470) medium supplemented with 1 ppm of 2,4-dichlorophenoxyacetic acid (2,4,-D) and 1% agar. The inoculated flasks were kept at 26°±1°C in 1500–1800 lux from incandescent light. The seeds took 4–6 days for germination. The seedlings when transferred in fresh RT medium formed thick roots with extensive root hair formation. These organised cultures were maintained for a period of 36 months after frequent subculturings in fresh RT medium and then transferred to RT liquid medium supplemented with 0.1 ppm of 2,4-D with no agar. The liquid cultures were grown on reciprocal horizontal shakers with strokes of 60 rpm and grown for 6 months after frequent subculturings of 4–6 weeks. The organised cultures were then harvested for extraction of insulin.

Hundred grams of the crushed tissues were homoganised in a Waring Belnder with 10 ml distilled water, 45 ml 95% ethanol and 3.6 ml concentrated sulfuric acid for 10–15 min at low speed and 25°–29°C. To this mixture 60 ml distilled water and 250 ml 95% ethanol were added and then homoganized for 15–20 min at low speed. Its pH was adjusted to 1.5–2.0 and the mixture was filtered in vacuo. The pH of the filtrate was adjusted to 3.0 with ammonium hydroxide (28%), mixed with 1.5 L cold absolute ethanol and 2 L diethyl ether and kept at 0.5° for 12 hr. A white flocculent precipitate (ppt) was obtained after decanting off the supernatant liquid. The crude ppt was washed first with 90 ml acetone, then with 30 ml anhydrous ether and dissolve in 25% ethanol buffered with ammonium hydroxide. Traces of zinc were added to this solution which was kept at room temperature for 18 hr. Colourless needle-like crystals were formed along with traces of zinc and other impurities. The crude crystals were dissolved in 25% ethanol buffered with ammonium hydroxide for analysis by tlc.

Thin glass plates (20 × 20 cm) coated (0.4 mm to 0.5 mm thick) with silica gel G (Kieselgel G nach Stahl; E. Merek) were activated at 100°C for half an hour. The solution containing the isolated substance was applied 1 cm above the edge of the plates along with the standard (insulin) and the plates were ran in an organic solvent mixture of n-butanol, water and acetic acid (125:2). The developed plates were dried at room temperature and sprayed with 0.25% ninhydrin in acetone. The ninhydrin possitive spots ($R_F = 0.19$) corresponding to insulin were isolated from about 200 unsprayed plates along with the silica gel G and extracted with absolute ethanol and ammonia (1:2). The extract was filtered and dried in vacuo. Pure colorless crystals thus obtained were weighed (1.90 gm/100 gram fresh weight of tissue).

The melting point of the purified compound (232°–235°) as well as the mmp (234°) were determined. The mp of the standard insulin was recorded as 233°.

The standard insulin as well as the isolated compound were hydrolyzed under reflux with 6N HCL for 20 hr separately. The hydrolyzates were filtered, dried, reconstituted separately in 50% ethanol and applied on strips of Whatman No. 1 paper. The paper strips were run in an organic solvent mixture of n-butanol, water and acetic acid (60:20:20). The hydrolyzates of both the isolated and the standard insulin were also applied separately along with the known amino acids (hydroxylasine, hydroxyproline, methionine and tryptophan). The various developed chromatograms were sprayed with 0.25% ninhydrin in acetone. The amino acids of the hydrolyzate of the standard coincided substantially exactly with that of the hydrolyzate of the isolated compound. Hydroxylsine, hydroxyproline, and tryptophan were found to be absent from the hydrolyzate of the isolated compound as well as the standard hydrolyzate which gave an indication that isolated compound is substantially identical with that of the insulin.

The IR spectrum (Perkin-Elmer 37 Grating, spectrophotometer using $COl_4$) of the isolated compound was superimposable with that of the standard.

The following are the advantages;
1. Animals will be saved from killing.
2. There will not be probability of any virus being carried along with insulin which may harm the human beings.
3. Any amount of insulin can be obtained by cultivating plants or cultures in vitro and thus it can be cheaper.
4. The antibodies will not be formed by administering plant insulin in human beings even if it is given in high doses.

We claim:

1. A process for isolating insulin from *Memordica charantia* Linn comprising extracting an organic material selected from the group consisting of cultures raised from seeds of *Memordica charantia* Linn and the fruit of *Memordica charantia* Linn with a mixture of ethanol, water and sulfuric acid, separating the extract from remaining material, adjusting the pH of said extract to 1.5 to 2.0 with ammonia or hydrochloric acid, adding cold ethanol and diethyl ether to precipitate insulin therefrom, adding zinc traces to the precipitate to crystallize the insulin as white crude crystals, and finally purifying the white crude crystals to white needle-like crystals.

2. A process as claimed in claim 1 wherein the fruit of *Memordica charantia* Linn is harvested during April, May or June.

3. A process as claimed in claim 1 wherein the cultures raised from seeds of *Memordica charantia* Linn are raised on revised Murashige and Skoog's medium (RT) supplemented with 2,4-dichlorophenoxyacetic acid and 1% agar.

4. A process as claimed in claim 3 wherein the cultures are grown for a period of 36 months and are then transferred to revised medium (RT) supplemented only with 2,4-dichlorophenoxyacetic acid and grown on reciprocal horizontal shakers having strokes of 60 rpm. at a temperature of 26° ± 1° C. in 1500–1800 lux obtained from an incandescent lamp for 4–6 months on frequent subculturings in fresh revised medium (RT).

5. A process as claimed in claim 1 wherein the extract after adding the cold ethanol and diethyl ether is maintained at 0.5° C. for 12 hours to precipitate insulin as a white flocculent material.

6. A process as claimed in claim 1 wherein the final purification step comprises dissolving the white crude crystals in 25% ethanol buffered with ammonium hydroxide, applying the solution to thin glass plates coated with activated silica gel G, developing the plates in n-butanol, water and acetic acid (12:5:2) drying the plates, extracting the insulin with 25% ethanol buffered with ammonium hydroxide, filtering the extract, and drying the filtrate to form white needle-like crystals.

* * * * *